United States Patent [19]

Guyton

[11] 4,105,303
[45] Aug. 8, 1978

[54] METHOD FOR DETERMINING THE REFRACTIVE CORRECTION FOR AN EYE

[76] Inventor: David L. Guyton, 10833 Willowisp, Houston, Tex. 77035

[21] Appl. No.: 756,933

[22] Filed: Jan. 5, 1977

[51] Int. Cl.² .............................................. A61B 3/00
[52] U.S. Cl. .................................................. 351/39
[58] Field of Search ........................................ 351/39

[56] References Cited

U.S. PATENT DOCUMENTS

| 3,822,932 | 7/1974 | Humphrey | 351/39 X |
| 3,947,097 | 3/1976 | Humphrey | 351/39 X |

Primary Examiner—Paul A. Sacher
Attorney, Agent, or Firm—Jeremiah J. Duggan; Allan H. Spencer

[57] ABSTRACT

An improved method is disclosed for determining the refractive correction for an eye. The method is an improvement over the method described by W. E. Humphrey in his U.S. Pat. No. 3,947,097. The improved method uses apparatus having only one variable astigmatic sub-system to achieve the same optical effects for which Humphrey specifically requires apparatus having two separate variable astigmatic sub-systems. The apparatus used is well-known in the art and includes variable spherical optics in combination with variable astigmatic optics, said variable astigmatic optics being equivalent to a rotatable, variable-power cross cylinder. Two stationary straight line targets, oriented in meridians substantially 45° from one another are alternately focused by the patient. To focus each straight line target the patient adjusts separately both sphere power and cross cylinder. Whenever the cross cylinder is adjusted, both the orientation and the power of the cross cylinder change as necessary to maintain the dioptric power of the cross cylinder acting in the meridian of the straight line target being focused. In the preferred embodiment of the method, the patient adjusts the orientation of the cross cylinder, and a servo mechanism adjusts the power of the cross cylinder as necessary. In an alternate embodiment, the patient adjusts the power of the cross cylinder, and a servo mechanism adjusts the orientation of the cross cylinder as necessary.

7 Claims, 19 Drawing Figures

METHOD FOR DETERMINING THE REFRACTIVE CORRECTION FOR AN EYE

BACKGROUND OF THE INVENTION

1. Field of the Invention

The invention relates generally to methods for determining the focal properties of a patient's eye, and relates more particularly to methods for determining the spherical and astigmatic refractive correction for a patient's eye.

2. Prior Art

U.S. Pat. Nos. 3,822,932 and 3,947,097 issued to W. E. Humphrey describe novel apparatus for determining the refractive correction for a patient's eye. In addition, U.S. Pat. No. 3,947,097 describes two basic embodiments of a method for using the described apparatus. Briefly, the apparatus and method allow the spherical and astigmatic portions of the refractive correction to be determined somewhat independently of one another. Furthermore, and most importantly, the astigmatic portion of the refractive correction is specifically determined as the combination of two astigmatic components which are measured independently of one another. Simple line targets with fixed orientations are used in the measurement process, greatly simplifying the patient's task. The patient is only required to judge the best focus of each line target as the correcting optical elements are varied.

One embodiment of Humphrey's method as described in U.S. Pat. No. 3,947,097 uses apparatus having a single variable astigmatic sub-system. This apparatus is used to measure the two astigmatic components successively and completely independently from one another. The complete astigmatic correction must then be calculated mathematically or graphically. This embodiment does not provide for optically generating or simulating the complete refractive correction whereby a corrected visual acuity may be obtained by the patient viewing a visual acuity chart through the simulated refractive correction.

The preferred embodiment of Humphrey's method as described in U.S. Pat. No. 3,947,097 uses apparatus which includes two separate variable astigmatic optical sub-systems which are used respectively to measure the two astigmatic components. This apparatus actually optically generates the complete refractive correction during the measurement process, allowing corrected visual acuity to be determined through the simulated refractive correction. This preferred embodiment of Humphrey's method is advantageous not only because visual acuity may be readily obtained, but also because the astigmatic refractive correction may be easily refined by convenient repetition of the steps in the measurement process. However, there are also disadvantages of Humphrey's preferred embodiment. Although the complete astigmatic correction is optically generated, to express this correction in conventional form still requires either mathematical or graphical calculation. In addition, subsequent arbitrary adjustment of the conventional form of the refractive correction cannot be accomplished without mathematical or graphical calculation to convert the arbitrary adjustment into the proper combination of adjustments for the two variable astigmatic sub-systems. Furthermore, apparatus having two separate variable astigmatic sub-systems is not common in the art. In addition to requiring an excessive number of optical elements, such apparatus tends to introduce additional optical aberrations, and for large refractive corrections the mathematical combination of the powers of the optical elements becomes non-linear. Certain aspects of Humphrey's preferred embodiment will later be described in detail.

There are thus several reasons why apparatus having a single variable astigmatic sub-system is preferable to apparatus having two separate such sub-systems. Examples of apparatus having a single variable astigmatic sub-system are numerous in the art. See, for example, U.S. Pat. No. 579,132 issued to F. M. Clark; U.S. Pat. No. 735,460 issued to W. L. Burnam; U.S. Pat. No. 1,070,631 issued to G. A. Rogers; Asher, H.M.F., Journal of Physiology 134:4P–5P (1956); and U.S. Pat. No. 3,664,631 issued to D. Guyton. Each apparatus of this type, in order to optically generate and simulate the complete refractive correction, includes means for rotating the variable astigmatic sub-system about the optical axis of the apparatus in order that the principal meridians of the astigmatic sub-system may be aligned with the principal meridians of the eye's astigmatic refractive error. Location of the principal meridians of the eye's astigmatic refractive error is difficult. Methods for locating these principal meridians often involve the use of targets difficult for the patient to interpret. Such methods are tedious for both the patient and the examiner.

Humphrey's method for determining the refractive correction, as described in his U.S. Pat. No. 3,947,097, uses exceedingly simple targets for the patient to interpret, that is, straight line targets with fixed orientations. The principal meridians of the eye's astigmatic error are not located initially but are located by calculation at the conclusion of the procedure. However, as stated previously, when Humphrey's method is used with apparatus having only one variable astigmatic sub-system, the complete refractive correction is not optically generated or simulated during the measurement procedure, but rather the complete refractive correction is mathematically calculated at the conclusion of the procedure. To obtain the patient's corrected visual acuity, the apparatus would have to be further adjusted to simulate the complete refractive correction according to the results of the mathematical calculations. Furthermore, when using apparatus having only one variable astigmatic sub-system. Humphrey provides no technique to further refine the refractive correction; the accuracy of the refractive correction may only be judged by repetition of the entire procedure.

SUMMARY OF THE INVENTION

Accordingly, it is an object of the present invention to provide an improvement in Humphrey's method for determining the refractive correction for a patient's eye. The improved method uses apparatus having only one variable astigmatic sub-system to achieve the same optical effects for which Humphrey specifically requires apparatus having two separate variable astigmatic sub-systems. Thus the improved method allows the use of simpler apparatus to obtain the same advantages which Humphrey achieves with more complicated apparatus.

In particular, the improved method of the present invention allows the use of simple line targets having fixed orientations; the complete refractive correction is actually optically generated and simulated during the measurement process, permitting determination of the corrected visual acuity; and the refractive correction may not only be rechecked but may be refined further by convenient repetition of any or all of the steps in the measurement process. An additional advantage is achieved with the improved method of the present invention; the complete astigmatic correction is known at the end of the measurement process without requiring additional mathematical or graphical calculation as is required in Humphrey's method.

Briefly, according to the improved method of the present invention, optical apparatus is used which includes variable spherical optics in combination with variable astigmatic optics, said variable astigmatic optics being equivalent to a rotatable, variable-power cross cylinder. A first straight line target of arbitrary and fixed orientation is presented. The variable cross cylinder is initially aligned with its principal meridians substantially 45° removed from the arbitrary orientation of the first straight line target. The patient adjusts separately both the sphere power and the cross cylinder power to optimize the focus of the first straight line target. A second straight line target is then presented, oriented substantially 45° away from the orientation of the first straight line target. The patient further adjusts separately both the sphere power and the cross cylinder to optimize the focus of the second straight line target, but this second adjustment of the cross cylinder occurs in a novel manner. That is, both the orientation and the power of the cross cylinder are adjusted substantially simultaneously in such a way as to maintain constant the power acting in the meridian of the second straight line target. (This optical manipulation produces the same effect as adjusting the second variable astigmatic sub-system in Humphrey's method of determining the refractive correction.) The refractive correction is thereby determined and is equal to the combination of the sphere and the cross cylinder.

Subsequently the refractive correction may be further refined by alternate re-focusing of the first and second straight line targets. For the re-focusing of each straight line target, the patient adjusts separately both the sphere power and the cross cylinder, with the cross cylinder being adjusted both in orientation and in power substantially simultaneously in such a way as to maintain constant the power acting in the meridian of the straight line target being focused.

The entire improved method of determining the refractive correction, including refinement, may be stated in terms of alternate focusing of the two straight line targets.

In the preferred embodiment of the improved method of the present invention, adjustment of the variable cross cylinder while holding the power constant in one meridian is accomplished by allowing the patient to adjust the orientation of the cross cylinder, and a servo mechanism automatically adjusts the power of the cross cylinder according to mathematical calculations to maintain constant the power acting in said one meridian.

In an alternate embodiment the patient adjusts the power of the cross cylinder, and a servo mechanism automatically adjusts the orientation of the cross cylinder according to mathematical calculations to maintain constant the power acting in said one meridian.

BRIEF DESCRIPTION OF THE DRAWINGS

Other objects, features, and advantages of the invention will be apparent from the following more detailed description of the invention wherein:

FIG. 18 (a) and (b) show alternate blocks for replacement in the flow diagram of FIG. 17, which replacement helps illustrate an alternate embodiment of the present invention.

DESCRIPTION OF PREFERRED EMBODIMENTS

Before stating the details of a preferred embodiment of the present invention, certain topics of prior art will be reviewed in detail in order to make clearer the basis for the present invention. These topics include conventions used in expressing refractive corrections, selected properties of cylindrical and crossed cylindrical lenses, and an analysis of Humphrey's method and apparatus for determining the refractive correction for an eye.

Figure 4:
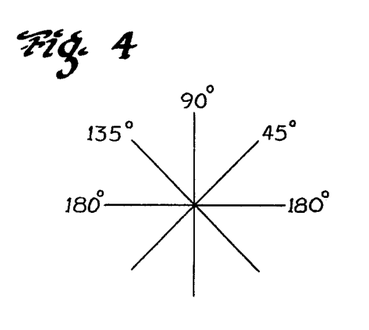
FIG. 4 is a diagram showing the degree notation conventionally used to identify the various meridians of a refractive correction.

The refractive correction for an eye is customarily expressed in term of a spherical lens (a "sphere") combined with a cylindrical lens (a "cylinder"), the cylinder having an axis oriented in a specified meridian. The degree convention used to designate meridians is shown in FIG. 4, as if looking at the patient's eye. Note that the 0° meridian is the same as the 180° meridian. For the horizontal meridian the designation 180° instead of 0° is preferred by convention.

Figure 5:
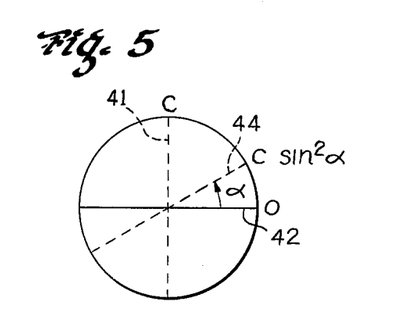
FIG. 5 is a diagrammatic illustration of a cylindrical lens showing the power acting in various meridians.

Referring to FIG. 5, the full power (C) of a cylindrical lens acts as indicated in meridian 41, 90° away from the axis meridian 42. Axis meridian 42 is shown in FIG. 5 as a solid line. The power acting in axis meridian 42 is zero, as indicated in FIG. 5. The cylindrical lens has power acting in the other meridians. For instance meridian 44 is an arbitrary meridian making an angle of $\alpha$ with the axis meridian 42. The power (P$\alpha$) acting in meridian 44 is indicated in FIG. 5 and is given by the close approximation: P$\alpha$ = (C) (SIN$^2\alpha$).

Figure 6:
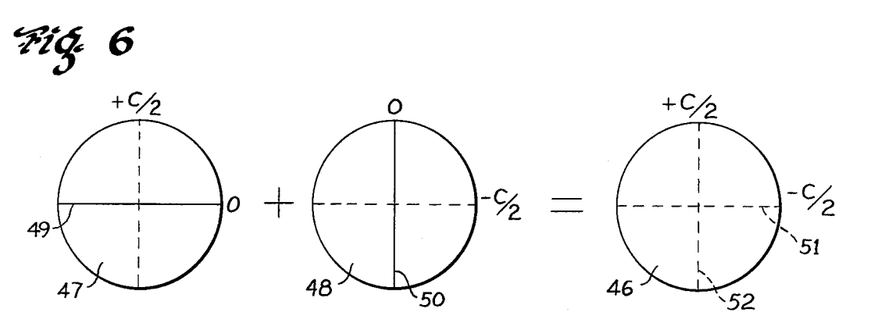
FIG. 6 is a diagrammatic illustration showing a cross cylinder being formed by the combination of two cylindrical lenses.

Referring to FIG. 6, a "cross cylinder" 46 is usually expressed (or generated) by the combination of two cylinders 47 and 48 having respective axes 49 and 50 disposed at right angles to one another. Cylinders 47 and 48 are of equal power but with opposite sign, cylinder 47 being plus and cylinder 48 being minus. If cylinders 47 and 48 are of opposite sign but are of unequal power, the combination is never referred to as a "cross cylinder." If the powers of cylinders 47 and 48 are designated as +C/2 and −C/2 respectively, the power acting in various meridians of these cylinders may be indicated as in FIG. 6. Meridian 51 of cross cylinder 46 is the axis meridian of the plus cylinder component, and meridian 52 is the axis meridian of the minus cylinder component. The powers acting in meridians 51 and 52 (powers −C/2 and +C/2 respectively) are indicated around the circumference of cross cylinder 46. Meridians 51 and 52 are known as the "principal" meridians of the resultant lens. The principal meridians of an astigmatic lens in general are always 90° apart and represent the meridians of greatest and least refractive power.

Figure 7:
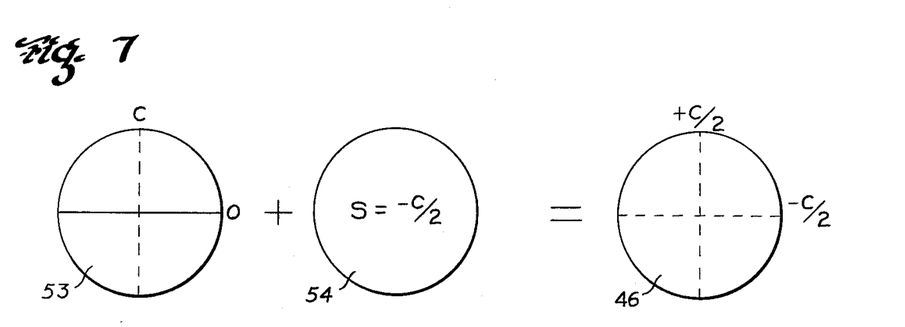
FIG. 7 is a diagrammatic illustration showing a cross cylinder being formed by the combination of a cylindrical lens with a spherical lens.

Referring to FIG. 7, the cross cylinder 46 from FIG. 6 may be equivalently expressed (or generated) by the combination of a cylinder 53 with a sphere 54. The power of cylinder 53 is C, and the power (S) of sphere 54 is equal to −C/2.

Figure 8:
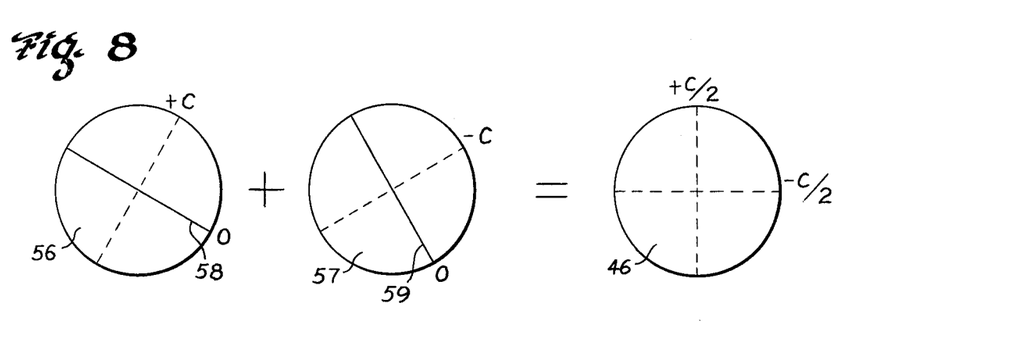
FIG. 8 is a diagrammatic illustration showing a cross cylinder being formed by two counter-rotatable cylindrical lenses.

Referring to FIG. 8, a third means of generating the cross cylinder 46 is schematically illustrated. Two cylinders 56 and 57 having equal power but opposite sign (+C and −C respectively) are combined with their respective axes 58 and 59 disposed at an angle ($\phi$ in FIG. 9) to one another. If $\phi$ has the appropriate value (100 = 30° for the example in FIG. 8), cross cylinder 46 will result from the combination.

Figure 9:
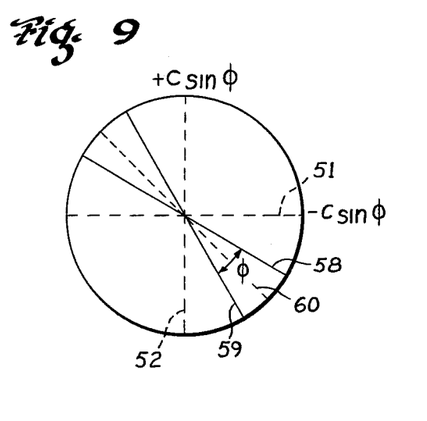
FIG. 9 is a diagram illustrating the sme combination as in FIG. 8, but in different form.

FIG. 9 shows in more general form the combination illustrated in FIG. 8. Cylinder axes 58 and 59 are shown having been rotated equal and opposite amounts away from meridian 60. This rotation produces a cross cylinder having principal meridians 51 and 52, meridians 51 and 52 each being 45° removed from meridian 60. The total angle between axes 58 and 59 is designated as $\phi$. The powers acting in principal meridians 51 and 52 are equal to −(C) (SIN $\phi$) and + (C) (SIN $\phi$) respectively. This relationship may be easily derived from the relationship P$\alpha$ = (C) (SIN$^2\alpha$), stated earlier for a single cylindrical lens.

The arrangement shown in FIGS. 8 and 9 of counter-rotating cylindrical lenses 56 and 57 is well-known in the art as a means of obtaining a variable-power cross cylinder. Strokes first described this arrangement in 1849, and the lens combination is commonly known as a Stokes lens.

Figure 10:
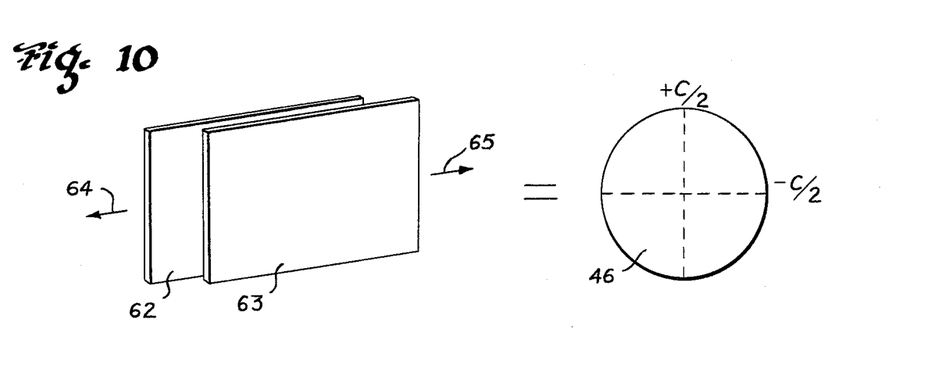
FIG. 10 is a diagrammatic illustration showing a cross cylinder being formed by the combination of two optical elements having complex optical surfaces.

Referring to FIG. 10, a fourth means of generating the cross cylinder 46 is schematically illustrated. Optical elements 62 and 63 having complex optical surfaces are arranged in such a manner that transverse movement of one with respect to the other (indicated by arrows 64 and 65) generates a variable-power cross cylinder. This arrangement is the subject of U.S. Pat. No. 3,751,138 issued to W. E. Humphrey. The nature of optical elements 62 and 63 (as well as the nature of related elements used to produce a variable-power sphere) may best be understood by referring to U.S. Pat. Nos. 3,305,294; 3,507,565; and 3,751,138.

Having reviewed various ways of expressing and of generating cross cylinders, it is now instructive to review certain optical properties of cross cylinders.

Figure 11:
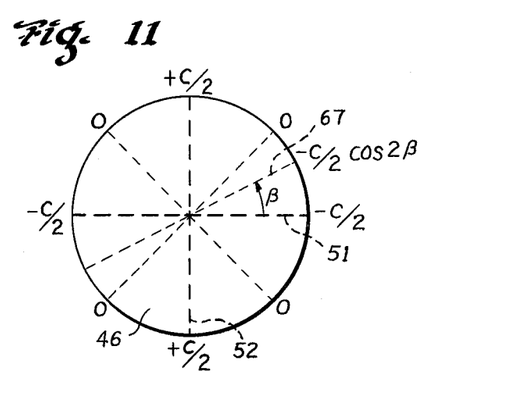
FIG. 11 is a diagrammatic illustration indicating the power acting in various meridians of a cross cylinder.

Referring to FIG. 11, cross cylinder 46 is schematically illustrated. Powers acting in various meridians of cross cylinder 46 are indicated around its circumference. As drawn, the horizontal meridian (180° meridian) is the axis meridian of the plus cylinder component. Arbitrary meridiant 67 makes an angle of $\beta$ with the axis meridian of the plus cylinder component. Again from the basic relationship P$\alpha$ = (C) (SIN$^2\alpha$) presented earlier for the case of a single cylindrical lens, the power acting in arbitrary meridian 67 of cross cylinder 46 may be shown to be equal to −(C/2) (COS 2$\beta$). Note that the power acting im each of the two meridians 45° away from the principal meridians is always zero. Again note that the powers acting in the two principal meridians are always equal but of opposite sign. The "power" of cross cylinder 46 as a whole is usually referred to as equal to ±C/2 diopters.

With reference to FIGS. 6, 7, 8, 9, and 10, it is instructive to review the equivalent ways in which the specified power of cross cylinder 46 may be changed. If the cross cylinder is generated by the combination of two cylinders with axes at right angles as in FIG. 6, the power of the cross cylinder may be changed simply by simultaneously increasing or decreasing the powers of the two cylinders, keeping the powers of the two cylinders equal but with opposite sign.

If the cross cylinder is generated by the combination of a cylinder with a sphere as in FIG. 7, the power of the cross cylinder may be changed by increasing or decreasing the power of the cylinder while simultaneously decreasing or increasing the power of the sphere, being certain that the sphere power is changed only half as much as the cylinder power and with the opposite sign. For example if the cylinder power is increased by 2 diopters, the sphere power must be changed by −1 diopters.

If the cross cylinder is generated by a Stokes lens as in FIGS. 8 and 9, the cross cylinder power is changed by counter-rotation of the component cylindrical lenses as explained previously. A variety of mountings and gear mechanisms are well-known in the art to accomplish such counter-rotation.

If the cross cylinder is generated by Humphrey's variable astigmatic optics as in FIG. 10, the cross cylinder power is changed by transverse movement of optical elements 62 and 63 with respect to one another.

It is important to note that rotation of principal meridians 51 and 52 of cross cylinder 46 to meridians other than the 180° and 90° meridians does not change the power of the cross cylinder, but simply changes the orientation of each meridian of the cross cylinder by the angular amount of said rotation.

Figure 12:
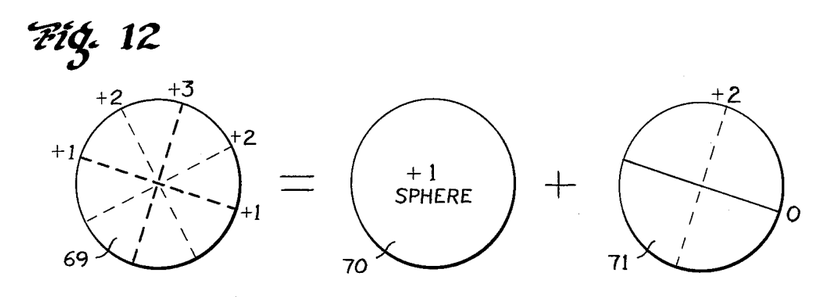
FIG. 12 is a diagrammatic illustration of a refractive correction being resolved into the combination of a sphere and a cylinder.
Figure 13:
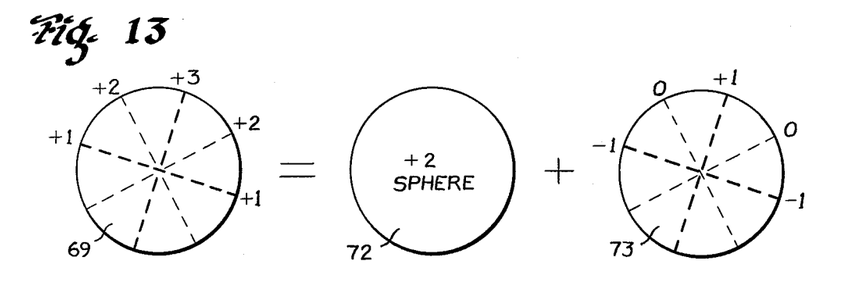
FIG. 13 is a diagrammatic illustration of the refractive correction of FIG. 12 being resolved into the combination of a sphere and a cross cylinder.

Having reviewed ways of generating and of varying the power of cross cylinders, it is now instructive to understand how cross cylinders may be used to help specify the refractive correction for a patient's eye. In FIG. 12, refractive correction 69 is customarily expressed as the combination of sphere 70 with cylinder 71, that is, +1.00 Sphere combined with +2.00 Cylinder with axis at 162°. FIG. 13 shows the same refractive correction 69 expressed as the combination of sphere 72 and cross cylinder 73, that is, +2.00 Sphere combined with +1.00 Cross cylinder with plus axis at 162°.

The +2.00 Sphere in FIG. 13 is known as the "spherical equivalent" of refractive correction 69, "spherical equivalent" being a term and concept well-known in ophthalmic optics. Note that the power of refractive correction 69 in the meridians 45° away from the principal meridians is +2 diopters, equal to the spherical equivalent. The spherical equivalent of refractive correction 69 is independent of the power or orientation of cross cylinder component 73. The cross cylinder component of an arbitrary refractive correction may be changed in power or rotated to any desired orientation without affecting the spherical equivalent of the refractive correction. The spherical equivalent may be thought of as the spherical portion of the refractive correction, and the cross cylinder may be thought of as the astigmatic portion of the refractive correction. In this form the spherical and astigmatic portions of the refractive correction may be conveniently determined and simulated independently of one another as shall be described presently.

Note in FIGS. 11 and 13 that the spherical equivalents of cross cylinders 46 and 73 are equal to zero. The spherical equivalent of every cross cylinder is equal to zero by definition. It is important to realize that combining a cross cylinder with an arbitrary lens does not change the spherical equivalent of that lens (because the spherical equivalent of the added cross cylinder is zero). For the same reasons, two or more cross cylinders may be combined with each other at arbitrary orientations, and the resultant will have a spherical equivalent of zero. The resultant of such a combination of cross cylinders will be, perhaps surprisingly, a simple cross cylinder. The principal meridians of this resultant will have powers and orientations calculatable by the "rules for combination of obliquely-crossed cylinders" which are well-known trigonometric relationships derived from the relationship $P\alpha = (C)(SIN^2\alpha)$ given previously for the case of a single cylindrical lens. Thus we can add, subtract, or rotate any number of cross cylinders as portions of a refractive correction without affecting the spherical equivalent of the refractive correction.

Figure 14:
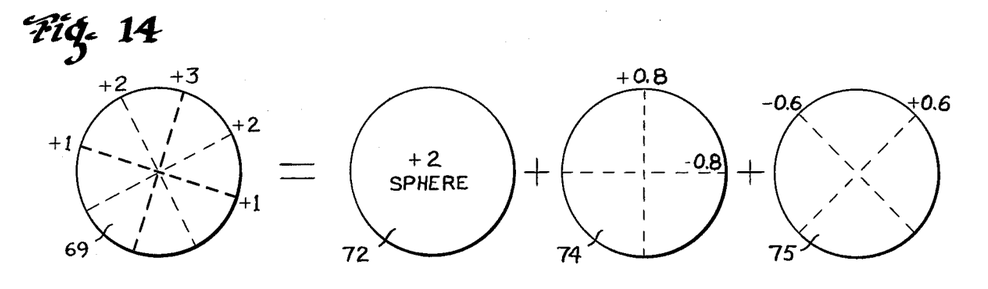
FIG. 14 is a diagrammatic illustration of the refractive correction of FIG. 12 being resolved into the combination of a sphere and two cross cylinders, where the two cross cylinders have fixed but different orientations.

For the same reasons that the combination of two or more cross cylinders is equal to a single cross cylinder, an arbitrary cross cylinder may be thought of as the resultant of two or more cross cylinders. For instance, cross cylinder 73 in FIG. 13 may be thought of as the resultant of cross cylinders 74 and 75 in FIG. 14. Cross cylinder 74 has principal meridians oriented purposefully at 180° and 90°. Cross cylinder 75 has principal meridians oriented purposefully at 45° and 135°. By altering the powers of these fixed-orientation cross cylinders 74 and 75, any power cross cylinder at any desired orientation may be generated. To obtain the equivalent cross cylinder to cross cylinder 73 of FIG. 13, the necessary powers of cross cylinders 74 and 75 have been calculated and are indicated around their circumferences. It should be evident from the arrangement in FIG. 14 that any given refractive correction may be generated by the combination of three elements: a sphere, a cross cylinder with principal meridians (or axes) at 180° and 90°, and a cross cylinder with principal meridians (or axes) at 45° and 135°. Such an arrangement is the subject of U.S. Pat. No. 3,822,932 issued to W. E. Humphrey. It should be noted that the principal meridians of the two fixed-orientation cross cylinders need not be 45° from one another, but as will be described later, this 45° relationship greatly simplifies Humphrey's method of determining the refractive correction.

Figure 1:
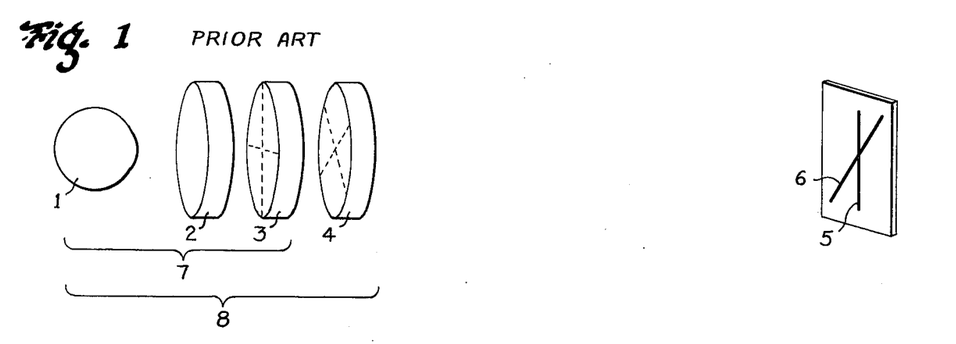
FIG. 1 is a diagrammatic perspective view of prior art apparatus for determining the refractive correction for an eye, which apparatus includes two variable astigmatic sub-systems.

Humphrey's method and apparatus for determining the refractive correction for an eye are the subjects of his U.S. Pat. No. 3,947,097. A preferred embodiment of his apparatus is schematically illustrated in FIG. 1 where the patient's eye 1 has an unknown refractive error. Three optical correcting elements are placed before the eye: variable spherical optics 2, variable-power cross cylinder 3 having principal meridians fixed at 180° and 90°, and variable-power cross cylinder 4 having principal meridians fixed at 45° and 135°. Through this combination of optical elements 2, 3, and 4, the patient views either straight line target 5 oriented in the 90° meridian or straight line target 6 oriented parallel to the 135° meridian, 45° away from straight line target 5. Only one of line targets 5 and 6 is shown to the patient at any given time.

Using the apparatus of FIG. 1, Humphrey's preferred method for determining the refractive correction for an eye may be briefly described as follows: The patient first views line target 6 and adjusts (STEP A) spherical optics 2 to focus line target 6 as best he can. Secondly the patient adjusts (STEP B) the power of variable cross cylinder 3 to further focus line target 6 as best he can. Line target 5 is now presented, and the patient readjusts (STEP C) spherical optics 2 as necessary to focus line target 5 as best he can. Finally the patient adjusts (STEP D) the power of variable cross cylinder 4 to further focus line target 5. The refractive correction has thereby been determined (except for possibly refining the refractive correction by repeating any or all of the above steps).

It is instructive to analyze what is accomplished optically by the steps of Humphrey's preferred method. Appropriate analysis of these steps will suggest an improvement in the method, said improvement being the subject of the present invention. In FIG. 1, let the powers of correcting elements 2, 3, and 4 all equal zero initially. Spherical optics 2 and variable cross cylinder 3 are first adjusted by the patient (STEPS A and B) to focus line target 6. A sharp focus of line target 6 is quickly and easily obtained by adjustment of elements 2 and 3. At this point the patient's eye 1 plus elements 2 and 3 should all three be considered together as a single optical system 7 viewing line target 6. This combined optical system 7 will, in the general case, be astigmatic, and yet straight line target 6 appears sharply in focus through this optical system. Now a straight line target may only be focused sharply by an astigmatic optical system if one of the principal meridians of the astigmatic optical system is parallel to the line target. Therefore it is evident that the adjustments of elements 2 and 3 by the patient (STEPS A and B respectively) serve in general to produce an astigmatic optical system 7 whose resultant principal meridians are now in a known orientation, namely oriented in the 45° and 135° meridians. This is the novel portion of Humphrey's method. The orientation of the principal meridians of the eye 1 are initially unknown. By using straight line target 6 having a fixed and purely arbitrary orientation, and by using variable optical elements 2 and 3 with the principal meridians of variable cross cylinder 3 being 45° away from the orientation of line target 6, an optical combination 7 is produced which includes the eye and which has principal meridians of known orientation, principal meridians parallel and perpendicular to line target 6.

After STEPS A and B of Humphrey's method are understood according to the preceding paragraph, STEPS C and D become obvious to those skilled in the art. The principal meridians of variable cross cylinder 4 have been purposefully fixedly aligned in the 45° and 135° meridians, that is, aligned exactly with the resultant principal meridians of optical system 7. Because of this alignment, any residual astigmatism in optical system 7 may be completely neutralized by appropriate adjustment of variable cross cylinder 4 (STEP D). Adjustment of elements 2 and 4 (STEPS C and D respectively) to focus line target 5 thus completes the determination of the refractive correction for eye 1, the refractive correction now being the combined sum of components 2, 3, and 4.

If the visual acuity obtained by the patient with the determined refractive correction is not as good as expected, it is possible to recheck or refine the refractive correction by repeating any or all of STEPS A, B, C, and D. Consider now the combination of eye 1 together with elements 2, 3, and 4 as a single system 8 viewing either line target 5 or line target 6. Line target 6 is always used when variable cross cylinder 3 is being adjusted, and line target 5 is always used when variable cross cylinder 4 is being adjusted. Repeat adjustments of variable sphere 2 and variable cross cylinder 3 are used to bring line target 6 into sharp focus (STEPS A and B repeated. Repeat adjustments of variable sphere 2 and variable cross cylinder 4 are used to bring line target 5 into sharp focus (STEPS C and D repeated). Again remember that a line target may only be focused sharply by an astigmatic optical system if one of the principal meridians of the optical system is parallel to the line target. Therefore if any residual astigmatism remains in optical system 8 after the focusing of line target 6 by variable elements 2 and 3, the principal meridians of this residual astigmatism must be oriented in the 45° and 135° meridians, correctly oriented for subsequent exact neutralization by variable cross cylinder 4 whose principal meridians are also in the 45° and 135° meridians. Likewise, if any residual astigmatism remains in optical system 8 after the focusing of line target 5 by variable elements 2 and 4, the principal meridians of this residual astigmatism must be oriented in the 180° and 90° meridians, correctly oriented for subsequent neutralization by readjustment of variable cross cylinder 3. The refractive correction for eye 1 may therefore be refined quite precisely be alternate focusing of line targets 6 and 5, line target 6 being focused by variable elements 2 and 3, and line target 5 being focused by variable elements 2 and 4.

It should be pointed out, as well-explained in Humphrey's U.S. Pat. No. 3,947,097, that STEPS A and B in the above method may be executed in reverse order without affecting the accuracy of the adjustments. The same is true for STEPS C and D. That is, when focusing either line target, the variable spherical optics may be adjusted first or the variable cross cylinder may be adjusted first; the end result is the same.

An important observation may now be made which allows an improvement in Humphrey's method, said improvement being the subject of the present invention. Referring back to FIG. 11, the powers acting in the various meridians of a cross cylinder are depicted. Note again that the power acting in each of the two meridians 45° away from the principal meridians of a cross cylinder is always zero, regardless of the power ($\pm C/2$) of the cross cylinder. Therefore, in FIG. 1 when the power of variable cross cylinder 3 is being adjusted, the powers acting in the 45° and 135° meridians of the entire optical system 8 remain constant. Likewise, when the power of variable cross cylinder 4 is being adjusted, the powers acting in the 180° and 90° meridians of the entire optical system 8 remain constant. The importance of this observation will become clearer as the method of the present invention is described in detail.

Having now reviewed in detail several topics of the prior art, a preferred embodiment of the present invention will be described.

Figure 2:
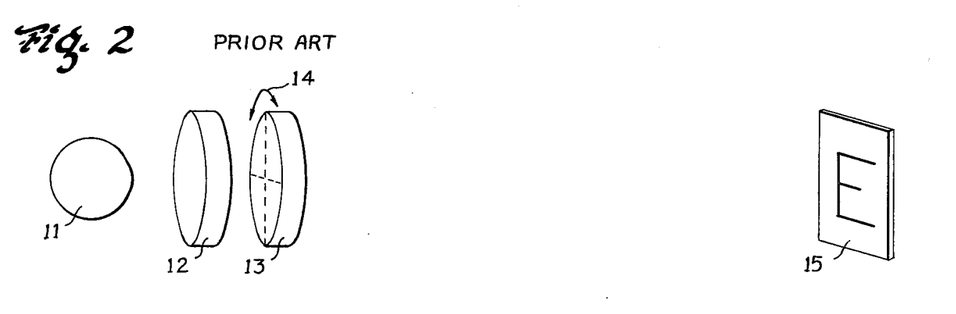
FIG. 2 is a diagrammatic perspective view of prior art apparatus for determining the refractive correction for an eye, which apparatus includes only one variable astigmatic sub-system.

The present invention constitutes an improvement in Humphrey's method for determining the refractive correction for an eye. This improved method is advantageous because it utilizes simple apparatus which is well-known in the art. In His U.S. Pat. Nos. 3,822,932 and 3,947,097, Humphrey specifically requires the use of separate first and second variable astigmatic optics in order to determine the refractive correction for an eye while at the same time generating and simulating the complete refractive correction. Examples of apparatus having two separate variable astigmatic optics are extremely rare in the art. The common apparatus well-known to the art consists of single variable astigmatic optics combined with variable spherical optics. For example, FIG. 2 illustrates schematically a variable-power cross cylinder 13, for example a Stokes lens, in combination with variable-power spherical optics 12 to provide the refractive correction for eye 11 relative to target 15. Variable spherical component 12 is usually in the form of a spherical optometer system, but may also represent individual trial lenses having different spherical powers. Variable cross cylinder 13 is rotatable about the optical axis as indicated by double arrow 14 to allow alignment of the principal meridians of cross cylinder 13 with the principal meridians of the eye 11. By a variety of methods well-known in the art, the principal meridians of eye 11 may be located, whereupon appropriate alignment and adjustment of variable cross cylinder 13 along with adjustment of variable spherical optics 12 may be used to generate and simulate the refractive correction for eye 11. Examples of the arrangement illustrated schematically in FIG. 2 may be found in U.S. Pat. No. 579,132 issued to F. M. Clark, U.S. Pat. No. 735,460 issued to W. L. Burnam, and in Asher, H. M. F., Journal of Physiology 134:4P–5P (1956).

The apparatus schematically illustrated in FIG. 2 requires fewer optical components than Humphrey's apparatus in FIG. 1 and requires less mathematical manipulation to yield the refractive correction in conventional form. However, there still may be certain practical shortcomings of the apparatus of FIG. 2: certain optical aberrations may be introduced by the variable-power cross cylinder 13; if the variable-power cross cylinder 13 is a Stokes lens, the change in power is non-linear with respect to the angular counter-rotation of its two component cylindrical lenses; and the astigmatic correction generated by element 13 may not always be accurately additive to the spherical correction generated by the spherical element 12 because of the physical separation between elements 12 and 13.

Figure 3:
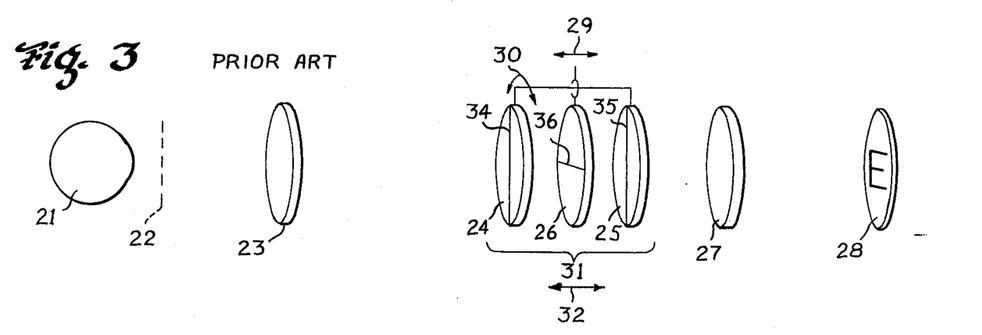
FIG. 3 is a diagrammatic perspective view of prior art apparatus for determining the refractive correction for an eye, which apparatus includes a preferred variable astigmatic sub-system.

Further apparatus is known to the art which overcomes these shortcomings and which is equally usable according to the improved method of the present invention. An example of such further apparatus is illustrated schematically in FIG. 3. The arrangement in FIG. 3 is fully described in U.S. Pat. No. 3,664,631 issued to D. Guyton. Briefly, light from target 28 is collimated by fixed spherical lens 27. The lens group 31 consists of three cylindrical lenses mounted together to be movable as a unit along the optical axis of the apparatus, that is, in the direction of double arrow 32. Lens group 31, receiving collimated light from lens 27, forms an image of target 28, which image moves according to double arrow 32 in fixed relation to the axial movement of lens group 31. The image formed by lens group 31 is re-imaged in the direction of the eye 21 by the spherical "optometer" lens 23. Optometer lens 23 is fixed in position a distance equal to its focal length from spectacle plane 22. As will be readily apparent from knowledge of the art, axial movement of lens group 31 simulates variable spherical power in spectacle plane 22. The spherical power (in diopters) simulated in spectacle plane 22 by this arrangement varies linearly with axis displacement of lens group 31. Cylindrical lenses 24 and 25 have their axes 34 and 35 respectively fixedly aligned with one another. The powers and the fixed spacing from one another of cylindrical lenses 24 and 25 are chosen such that the combination of lenses 24 and 25 has an equivalent focal length equal to the focal length of cylindrical lens 26. Cylindrical lens 26 is moveable axially within lens group 31 as indicated by double arrow 29. Axis 36 of cylindrical lens 26 is fixed at right angles to the common axis orientation of lenses 24 and 25. Axial movement of lens 26 alone in the direction of double arrow 29 produces a variation in the simulated cylindrical power acting in spectacle plane 22. The simulated cylinder may either have plus power or minus power, but its axis is always parallel to axis 36 or lens 26. The cylindrical power (in diopters) simulated in spectacle plane 22 by this arrangement varies linearly with axial displacement of lens 26. Lens group 31 may also be rotated as a unit about the optical axis as indicated by double arrow 30. By this means the principal meridians of lens group 31 may be aligned with the principal meridians of eye 21.

The arrangement of FIG. 3 thus is capable of generating variable sphere, variable cylinder, and variable axis orientation by appropriate movement of its parts. It should be obvious that variable-power cross cylinder may be obtained by linking the variable sphere movement with the variable cylinder movement such that the cylinder changes twice as fast as the sphere but with the opposite sign. For example in FIG. 3 if cylindrical lens 26 moves twice as far to the right (relative to lens group 31) as the entire lens group 31 moves to the left, a change in cross cylinder is accomplished without changing the spherical equivalent of the simulated refractive correction in spectacle plane 22.

The arrangement of FIG. 3 introduces fewer optical aberrations than the usual apparatus represented by FIG. 2, dioptric powers change linearly with movement of the parts, and the additivity problem is not present. Otherwise the arrangement of FIG. 3 may be considered equivalent to that of FIG. 2, that is, consisting of a variable spherical portion in combination with a rotatable, variable-power cross cylinder portion. For ease of explanation, the arrangement of FIG. 2 will be used to illustrate the improved method of the present invention, but from the above explanation it should be evident that other forms of apparatus known to the art, including the arrangement of FIG. 3, may be used equally as well if not to even greater advantage.

Figure 15:
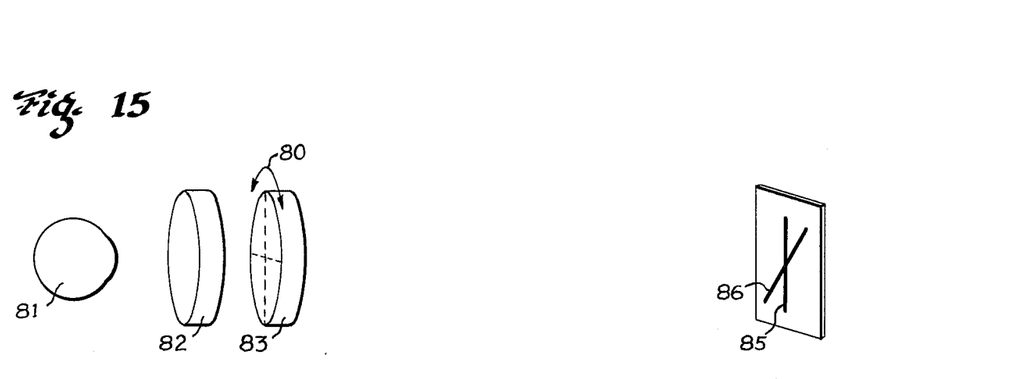
FIG. 15 is a diagrammatic perspective view of apparatus for determining the refractive correction for an eye according to the improved method of the present invention.

Having reviewed the apparatus involved, the improved method of the present invention will now be described. FIG. 15 shows an optical arrangement identical to the arrangement of FIG. 2 except that target 15 in FIG. 2 has been replaced by line targets 85 and 86 in FIG. 15. Line targets 85 and 86 are identical to, and serve the same purpose as, line targets 5 and 6 in FIG. 1. Only one of line targets 85 and 86 is viewed at any one time.

The first three steps in the improved refracting method are identical to the first three steps of Humphrey's method (STEPS A, B, and C). That is, the patient first views line target 86 (oriented here in the 135° meridian, looking toward the patient) and adjusts (STEP A) spherical optics 82 to optimize the focus of line target 86. Secondly the patient adjusts (STEP B) the power of variable cross cylinder 83 (with principal meridians oriented initially in the 180° and 90° meridians) to further optimize the focus of line target 86. Line target 85 is now presented, and the patient re-adjusts (STEP C) spherical optics 82 as necessary to optimize the focus of line target 85. The last step in the Humphrey method (STEP D) requires focusing line target 85 with a second variable cross cylinder with axes fixed at 45° and 135°. To avoid having to provide this second variable cross cylinder, the present invention provides the necessary method to vary substantially simultaneously the power and principal meridian orientation of variable cross cylinder 83 to accomplish exactly the same optical effect as would be accomplished by adjusting the power of the second variable cross cylinder of Humphrey's method. This "second" adjustment of variable cross cylinder 83 is accomplished without losing the information derived from the first adjustment (STEP B) of variable cross cylinder 83.

At the conclusion of this "second" adjustment of variable cross cylinder 83, the power and principal meridian orientation of variable cross cylinder 83 represent the astigmatic correction for eye 81. This correction is the same correction as would have been obtained by the combined effect of variable cross cylinders 3 and 4 of FIG. 1 adjusted according to Humphrey's method. From the additive properties of cross cylinders that were reviewed earlier, it is obvious that the combination of variable cross cylinders 3 and 4 of FIG. 1 may always be equivalently represented by a single cross cylinder such as variable cross cylinder 83 in FIG. 15, provided that both the power and principal meridian orientation of variable cross cylinder 83 are properly chosen. What is not obvious is how cross cylinder 83 may undergo a "second" to simulate the adjustment of variable cross cylinder 4 of FIG. 1.

To further describe the improved method of the present invention, an important observation stated earlier must be repeated. The power acting in each of the two meridians 45° away from the principal meridians of a variable-power cross cylinder is always zero, regardless of the adjusted power of the variable-power cross cylinder, as illustrated in FIG. 11. Therefore in FIG. 1 when the power of variable cross cylinder 4 is being adjusted, the powers acting in the 180° and 90° meridians of the entire optical system 8 remain constant. This observation, when extended to the arrangement of FIG. 15, requires that when the "second" adjustment of variable cross cylinder 83 is performed (in order to focus line target 85), the powers of variable cross cylinder 83 acting in the 180° and 90° meridians must remain constant. To vary the power of variable cross cylinder 83 while holding the powers acting in the 180° and 90° meridians constant, the principal meridian orientation of cross cylinder 83 must change simultaneouly with the power change of variable cross cylinder 83. This is preferably accomplished by allowing the patient to adjust the principal meridian orientation of cross cylinder 83 while a servo mechanism automatically adjusts the power of variable cross cylinder 83 to maintain constant the power acting in either the 90° meridian or the 180° meridian. (In a cross cylinder, the power acting in any meridian is always equal, but of opposite sign, to the power acting 90° away; therefore holding the power constant in either the 90° meridian or the 180° meridian automatically holds the power constant in both of these meridians. In describing the improved method of the present invention, the chosen meridian in which power will be held constant during cross cylinder adjustment will henceforth always be specified as that meridian which is parallel to the orientation of the line target being focused.)

Figure 16:
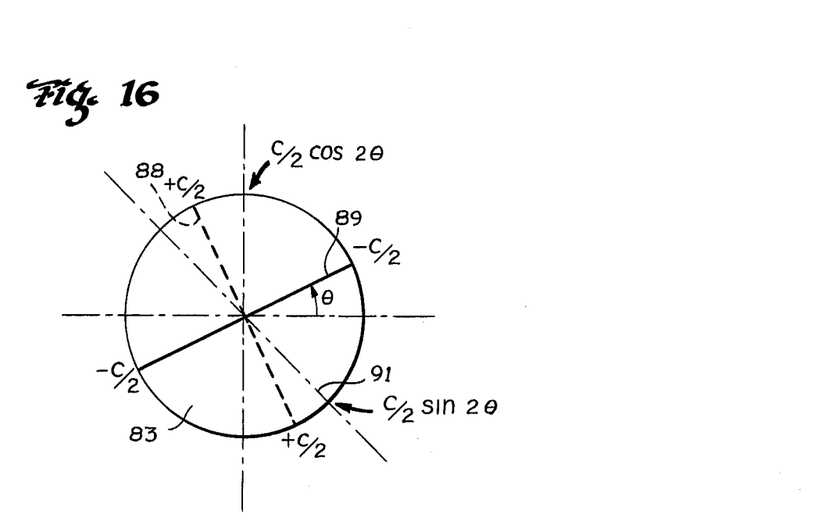
FIG. 16 is a diagrammatic illustration indicating the power acting in various meridians of a cross cylinder, with the cross cylinder having an arbitrary orientation.

To hold constant the power acting in the 90° meridian of variable cross cylinder 83, this power must first be determined. FIG. 11 shows the power acting in arbitrary meridian 67 of cross cylinder 46. Using this relationship, the diagram in FIG. 16 may be obtained. Variable cross cylinder 83 is shown having a power of ±C/2 diopters with principal meridians 88 and 89. To specify the orientation of variable cross cylinder 83 with respect to the 180° meridian, one of the principal meridians 88 or 89 must be chosen. Principal meridian 89 has been chosen and is therefore indicated by a solid line. The angle by which principal meridian 89 has been rotated from the 180° meridian is indicated by $\theta$ ($\theta$ is positive if measured counterclockwise from the 180° meridian, negative if measured clockwise from the 180° meridian). From the relationship in FIG. 11 it is readily apparent in FIG. 16 that the power of variable cross cylinder 83 acting in the 90° meridian is equal to (C/2) (COS $2\theta$), as indicated. Later it will be necessary to know the power acting in meridian 91, the 135° meridian. This power is equal to (C/2) (COS $2(\theta-45°)$), or (C/2) (SIN $2\theta$), as indicated in FIG. 16. It should be stated that during variation of the power of variable cross cylinder 83 in FIG. 16, the value of C/2 may be made either positive or negative. For example, the power acting in principal meridian 89 may be made either negative or positive, and the mathematical relationships shown in FIG. 16 will still be valid. To avoid ambiguity, the "power of cross cylinder 83" will henceforth be designated as equal to C/2. C/2 will actually be the power acting in principal meridian 88, perpendicular to principal meridian 89. C/2 may become either positive or negative during the various adjustments of cross cylinder 83.

Using the convention for angular orientation adopted in FIG. 16, the basic steps of the improved method of the present invention will now be restated in greater detail, referring back to FIG. 15. The patient first adjusts variable spherical optics 82 and variable cross cylinder 83 to focus line target 86. (Variable cross cylinder 83 is initially oriented with principal meridians at 180° and 90°, that is with $\theta = 0°$.) Line target 85 is then introduced, replacing line target 86, and the patient re-adjusts variable spherical optics 82 to obtain the best focus possible for line target 85. The power (designated "P") acting in the 90° meridian of variable cross cylinder 83 is now calculated (P = (C/2) (COS $2\theta$)), and the value of P is stored in conventional cumputer memory. Note that the 90° meridian is the meridian parallel to the orientation of line target 85, the line target being focused. The patient now varies the orientation of variable cross cylinder 83 (adjusts $\theta$) to optimize the focus of line target 85. As $\theta$ changes, and as the patient is focusing line target 85, the power acting in the 90° meridian must remain constant. For this condition to be met, the necessary power (C/2) of cross cylinder 83 is continually calculated as $\theta$ is changed (C/2 = P/COS $2\theta$), and the power of cross cylinder 83 is automatically changed to follow the calculated C/2 value, the changes in orientation ($\theta$) and power (C/2) of cross cylinder 83 thus occuring substantially simultaneously. The mechanism required for automatically adjusting the power of cross cylinder 83 to follow the calculated C/2 value is a standard servo mechanism, well-known to the art, and need not be further described here.

When line target 85 is brought into focus by this novel re-adjustment of variable cross cylinder 83, the refractive correction for eye 81 will be determined. The refractive correction consists of the combination of spherical optics 82 (of power "S") with cross cylinder 83. In standard notation, the refractive correction would be described as "(S-(C/2)) diopters Sphere combined with C diopters Cylinder at axis $\theta$."

If the visual acuity obtained by the patient with the determined refractive correction is not as good as expected, it is possible to recheck or refine the refractive correction by repeating any or all of the basic steps. That is, line target 86 in FIG. 15 may be focused again by adjustments of spherical optics 82 and variable cross cylinder 83, and line target 85 may be focused again by adjustments of spherical optics 82 and variable cross cylinder 83. When line target 86 is being re-focused by adjusting variable cross cylinder 83, the powers of cross cylinder 83 acting in the 45° and 135° meridians must remain constant. This may be accomplished by first calculating the initial power (designated "Q") acting in the 135° meridian of variable cross cylinder 83. Note that the 135° meridian is the meridian parallel to the orientation of line target 86. FIG. 16 indicates that Q = (C/2) (SIN $2\theta$). As the patient adjusts the orientation of cross cylinder 83 (adjusts $\theta$) to focus line target 86, the power (C/2) of cross cylinder 83 is automatically changed such that C/2 = Q/SIN $2\theta$. (Holding the power in the 135° meridian constant is thus accomplished in a similar manner as when previously holding the power acting in the 90° meridian constant.)

To continue in refining the refractive correction, line target 85 may be re-introduced, whereupon variable spherical optics 82 and variable cross cylinder 83 are re-adjusted to optimize the focus of line target 85. As variable cross cylinder 83 is re-adjusted, the power acting in the meridian parallel to line target 85 (the 90° meridian) is maintained constant by the means previously described.

Thus the refractive correction is rechecked or refined again and again if desired, simply by alternate re-focusing of lines 85 and 86 in the above prescribed manner. Continued refinement is usually not necessary, for an accurate refractive correction is usually quickly determined.

Figure 17:
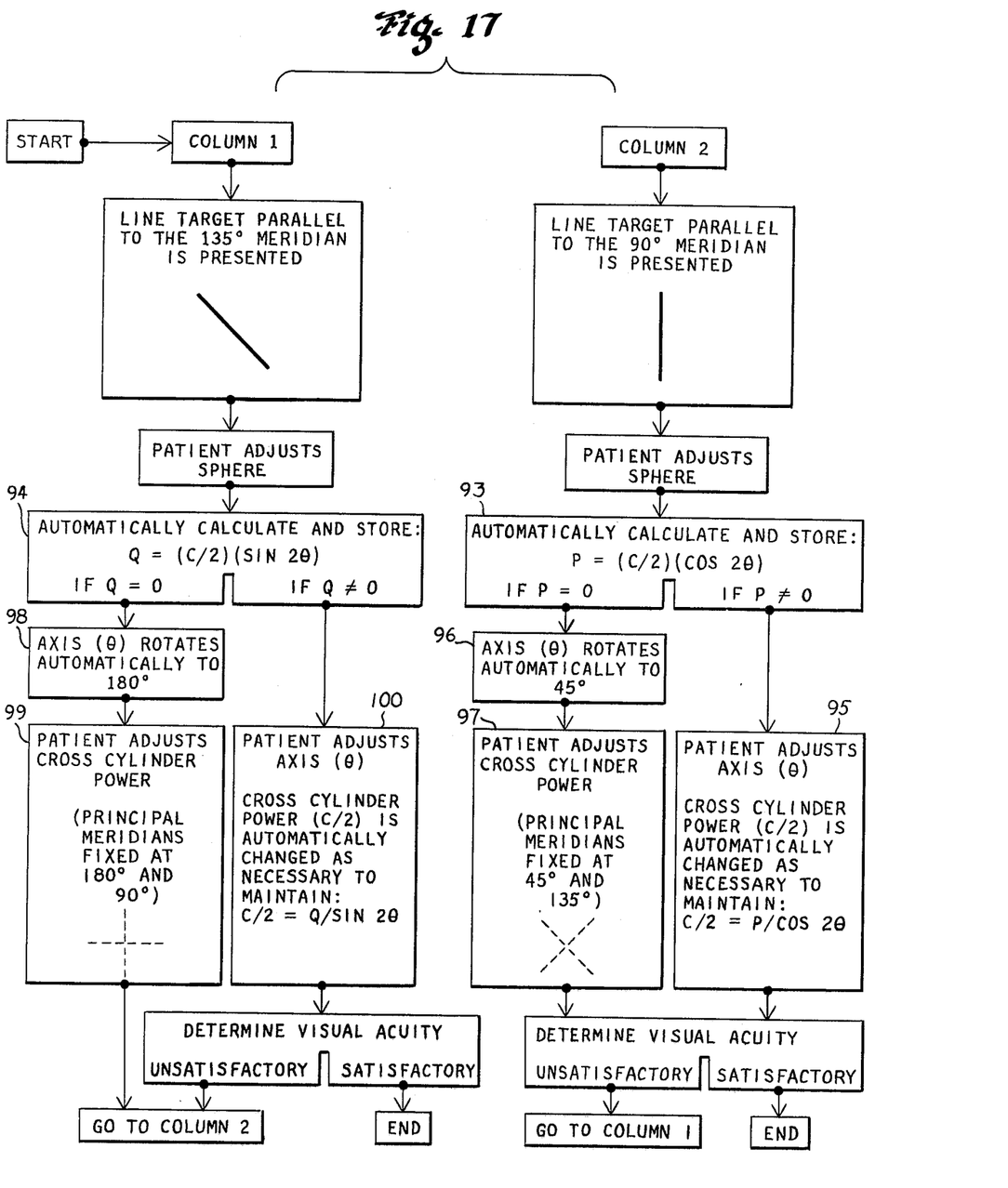
FIG. 17 is a flow diagram including the steps of the preferred embodiment of the present invention.

FIG. 17 is a flow diagram including the various steps of the preferred embodiment of the present invention. The flow diagram is mostly self-explanatory in view of the preceding discussion; however, certain aspects require further explanation. Values for "P" and for "Q" are calculated within blocks 93 and 94 respectively. If the calculated value for P should ever equal zero, the calculated value P/COS $2\theta$ will also equal zero, and the cross cylinder power (C/2) will not change as $\theta$ is varied according to the step in block 95. Therefore an alternate pathway is provided (blocks 96 and 97) if P equals zero. The alternate pathway for cross cylinder adjustment (blocks 96 and 97) must still obey the condition that the power acting in the meridian parallel to the line target remains constant. Both the orientation and the power of the cross cylinder may change as necessary to maintain constant the power acting in this case in the 90° meridian. Whenever P equals zero, the orientation of the cross cylinder must specifically not be allowed to change during the adjustment, but rather the cross cylinder must be fixed with principal meridians oriented in the 45° and 135° meridians (block 96: "Axis ($\theta$) rotates automatically to 45°"). The power of the cross cylinder is then directly adjusted by the patient (block 97) to focus the line target oriented in the 90° meridian. Because the power of a cross cylinder acting in the meridians 45° away from its principal meridians is always zero, the power acting in the 90° meridian remains constant as required, validating the alternate pathway represented by blocks 96 and 97. A similar alternate pathway (blocks 98 and 99) is necessary if Q should ever equal zero, as illustrated in the flow diagram.

The flow diagram of FIG. 17 is valid even for random initial powers and orientations of correcting elements 82 and 83 of FIG. 15. In the usual case, however, the initial values will be S = 0, C/2 = 0, and $\theta$ = 0°. The improved method of determining the refractive correction for an eye begins at the top of COLUMN 1 in FIG. 17. The patient first adjusts sphere to optimize the focus of the line target at 135°. Because C/2 will usually be zero at this point, Q will equal zero, and the left-hand pathway of COLUMN 1 will be followed with the patient adjusting cross cylinder power in the 180° and 90° meridians to further focus the line target at 135°. COLUMN 2 is then followed with the patient adjusting sphere to best focus the line target at 90°. P will usually not equal zero, and the right-hand pathway of COLUMN 2 will be followed. The patient will adjust axis ($\theta$) while the cross cylinder power (C/2) is automatically changed to maintain C/2 = P/COS $2\theta$, that is, to maintain constant the power acting in the meridian parallel to the line target which is being focused. Visual acuity will be determined, and if the visual acuity is satisfactory, the refractive correction will have been determined. If the visual acuity is unsatisfactory, COLUMN 1 will again be followed, this time with Q usually not equal to zero, and the right-hand pathway of COLUMN 1 will be followed — and so forth according to the flow diagram.

The flow diagram of FIG. 17 may be altered by certain rearrangements or additions within the spirit of the invention. For instance, the adjustment of sphere may be made after instead of before the adjustment of cross cylinder power in either or both COLUMN 1 and COLUMN 2. Also after final determination of a satisfactory visual acuity, a frequently added step is a final adjustment of sphere using a visual acuity chart as a target. A visual acuity chart used with the common "fogging" technique, well-known to the art, serves to relax the patient's accommodation and results in a more accurate value for the final spherical portion of the refractive correction. This "fogging" step is not always necessary and was omitted from the flow diagram for the sake of simplicity.

It should also be pointed out that the determination of the refractive correction may also begin at the top of COLUMN 2 rather than at the top of COLUMN 1 in FIG. 17. In addition, a straight line target oriented at 45° may be used in place of the line target oriented at 135°, and a line target oriented at 180° may be used in place of the line target oriented at 90°.

Other types of line targets known to the art may be used. For example in FIG. 15 it will be recalled that either line target 85 or 86 may only be focused sharply when it is parallel to a principal meridian of the optical system viewing it. In FIG. 15 the optical system viewing either line target 85 or 86 is the combination of eye 81 with correcting elements 82 and 83. Other types of line targets which are specially designed to indicate the condition of being non-parallel to a principal meridian ("axis error") may be used to advantage in place of line targets 85 and 86 when performing cross cylinder adjustment. Examples of such specialized line targets are the "astigmatic array targets" described in U.S. Pat. Nos. 3,785,723 and 3,841,760 issued to D. L. Guyton.

In the preferred embodiment of the present invention as diagrammed by FIG. 17, the steps in blocks 95 and 100 involve varying the orientation and power of a variable cross cylinder (such as variable cross cylinder 83 in FIG. 15) while holding the power acting in a specified meridian constant. For the preferred embodiment of the present invention it has been chosen to allow the patient to adjust the orientation of the cross cylinder while a servo mechanism adjusts the power of the cross cylinder to maintain the power acting in the specified meridian constant. In an alternate embodiment of the present invention the patient adjusts the power of the cross cylinder while a servo mechanism adjusts the orientation of the cross cylinder to accomplish the same end result, the power acting in the specified meridian is maintained constant. FIG. 17 may be used to illustrate this alternate embodiment if blocks 95 and 100 of FIG. 17 are replaced respectively by blocks 95' and 100' shown as FIGS. 18 (a) and 18 (b). The steps in blocks 95' and 100' involve the ARCCOSINE and ARCSINE functions. These functions in general introduce ambiguity. For example, ARCCOS (0.5) may be either +60° or −60°, and −60° is equivalent to +120° in the meridian notation conventionally used for refractive corrections (see FIG. 4). The usual convention to avoid this ambiguity is to specify the "principal value" of the ARCCOSINE and ARCSINE functions. The range of principal values for the ARCCOSINE function is 0° to 180°. The range of principal values for the ARCSINE function is −90° to +90°. Using only the principal values for these functions avoids ambiguity, but in the present application it is frequently the non-principal value that is the correct one. Therefore several steps are necessary within each of blocks 95' and 100' to provide the correct result.

Figure 18A:
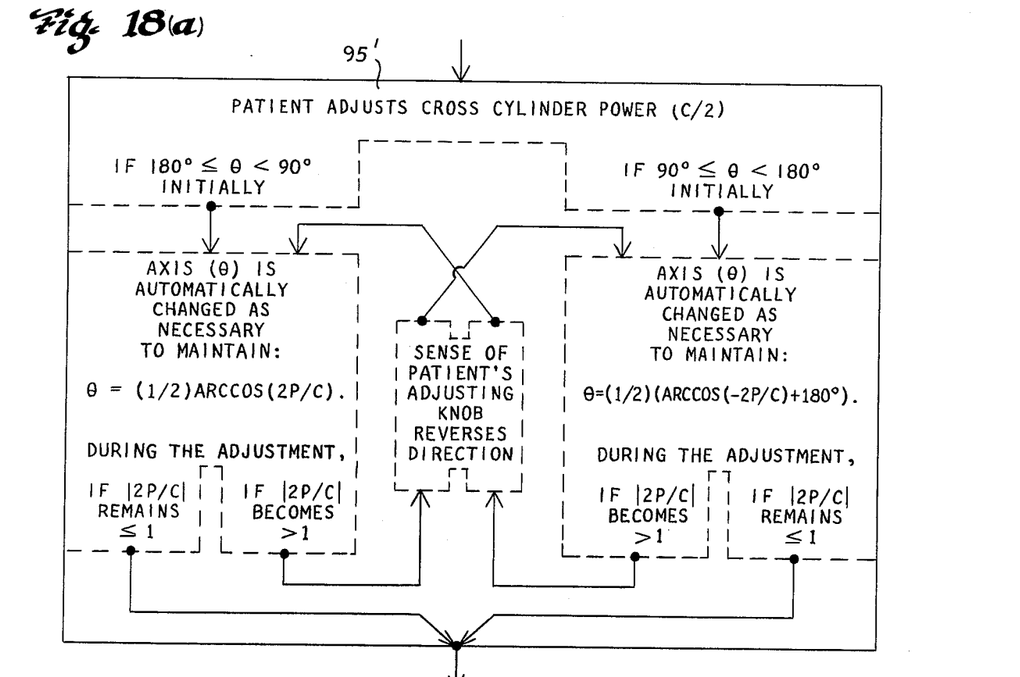

In block 95' the patient adjusts the cross cylinder power (C/2). Axis ($\theta$) is changed automatically to maintain constant the power (P) acting in the 90° meridian. If θ is initially less than 90°, the principal value of the ARCCOSINE function is the desired value, and θ is changed automatically to follow the calculated value: $\theta = (\frac{1}{2}) \text{ARCCOS}(2P/C)$. If θ is initially greater than 90°, the non-principal value of the ARCCOSINE function is the desired value, and θ is changed automatically to follow the calculated value: $\theta = (\frac{1}{2})(\text{ARCCOS}(-2P/C) + 180°)$, which uses by mathematical manipulation the desired non-principal value of the ARCCOSINE function. If θ is initially 180° or 90°, either the principal value or the non-principal value of the ARCCOSINE function is correct. In block 95′, if θ is initially 180°, the principal value of the ARCCOSINE is used arbitrarily; if θ is initially 90°, the non-principal value of the ARCCOSINE function is used arbitrarily.

A further manipulation is necessary within block 95′. If the cross cylinder power (C/2) is adjusted by the patient to be less than P, which will easily and frequently occur, the value [2P/C] will be greater than 1, and the ARCCOSINE function is not defined for arguments greater than 1. Therefore if the value [2P/C] becomes greater than 1 as the patient turns a knob to adjust the cross cylinder power (C/2), either the patient must immediately be made to reverse the direction he is turning the knob, or else the sense of the adjusting knob itself must suddenly reverse direction. To avoid patient confusion, it has been arbitrarily chosen in block 95′ to automatically reverse the direction of the sense of the patient's knob whenever [2P/C] becomes greater than 1. Whenever the sense of the patient's adjusting knob is reversed, it is also necessary to begin using the opposite value for the ARCCOSINE function. That is, if the principal value is being used before the sense of the patient's adjusting knob is reversed, the non-principal value is necessary after the sense is reversed, and vice-versa. Careful study of the flow diagram within block 95′ will help make these manipulations clearer, but the reasons why these manipulations are necessary will not be fully appreciated until numerical examples are worked through.

Figure 18B:
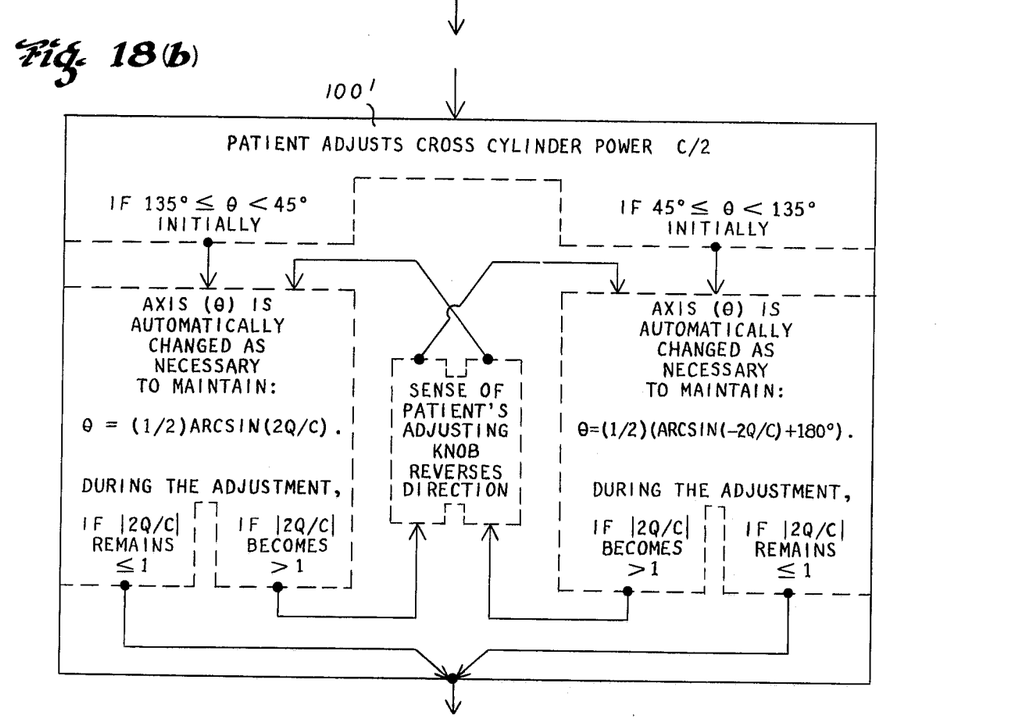

Analogous manipulations to those in block 95′ are necessary within block 100′ in FIG. 18 (b). Careful study of the flow diagram within block 100′ and the working through of numerical examples will make these manipulations clear.

The manipulations within blocks 95′ and 100′ are more complicated than the manipulations within blocks 95 and 100 of FIG. 17. The preferred embodiment of the present invention incorporates blocks 95 and 100, while the alternate embodiment incorporates blocks 95′ and 100′. Both embodiments are equally valid and accomplish the same end result as explained earlier.

Finally, as pointed out earlier, the improved method of the present invention may be used with a variety of apparatus well-known to the art. Apparatus having stepwise-variable dioptric power may be used as well as apparatus having continuously-variable dioptric power. In addition, the improved method of the present invention may be easily adapted to determining the refractive correction for a variety of optical systems not limited to a patient's eye.

What is claimed is:

1. A method for determining the refractive correction for an eye including the steps of:
   providing corrective optics between a patient's eye and a target location, said corrective optics comprising variable spherical optics in combination with variable astigmatic optics, said variable astigmatic optics being equivalent to a cross cylinder having variable power and variable orientation;
   providing, in alternate succession, first and second straight line targets in said target location, said first straight line target having arbitrary meridional orientation without regard to any suspected principal meridian of the astigmatism of the patient's eye, and said second straight line target having meridional orientation substantially 45° away from the orientation of said first straight line target;
   adjusting separately, for each of said straight line targets, both said variable spherical optics and said variable astigmatic optics to optimize the focus of the straight line target within the patient's eye;
wherein the improvement comprises:
   allowing the initial power and orientation of said variable astigmatic optics to have arbitrary values prior to the focusing of said first straight line target;
   maintaining the power and orientation of said variable astigmatic optics at the successive adjusted values prior to the focusing of each successive straight line target;
   and accomplishing the adjustment of said variable astigmatic optics for each of said straight line targets by adjusting both the orientation and the power of the variable astigmatic optics substantially simultaneously as necessary to maintain constant the dioptric power then acting in the meridian parallel to the orientation of the straight line target being focused;
whereby said refractive correction is determined.

2. The method according to claim 1 and wherein said substantially simultaneous adjustment of the orientation and the power of the variable astigmatic optics is accomplished by the patient adjusting the orientation of the variable astigmatic optics and a servo mechanism adjusting the power of the variable astigmatic optics.

3. The method according to claim 1 and wherein said substantially simultaneous adjustment of the orientation and power of the variable astigmatic optics is accomplished by the patient adjusting the power of the astigmatic optics and a servo mechanism adjusting the orientation of the variable astigmatic optics.

4. A method for determining the refractive correction for an eye including the steps of:
   providing corrective optics between a patient's eye and a target location, said corrective optics comprising variable spherical optics in combination with variable astigmatic optics, said variable astigmatic optics being equivalent to a cross cylinder having variable power and variable orientation;
   providing a first straight line target in said target location, said first straight line target having arbitrary meridional orientation without regard to any suspected principal meridian of the astigmatism of the patient's eye;
   orienting the principal meridians of said variable astigmatic optics substantially 45° away from the orientation of said first straight line target;
   adjusting separately both said variable spherical optics and the power of said variable astigmatic optics to optimize the focus of said first straight line target within the patient's eye;
   replacing said first straight line target by a second straight line target in said target location, said second straight line target having meridional orientation substantially 45° away from the orientation of said first straight line target;

wherein the improvement comprises:

further adjusting separately both said variable spherical optics and said variable astigmatic optics to optimize the focus of said second straight line target within the patient's eye, said further adjustment of the variable astigmatic optics being accomplished by adjusting both the orientation and the power of the variable astigmatic optics substantially simultaneously as necessary to maintain constant the dioptric power acting in the meridian parallel to the orientation of said second straight line target;

whereby said refractive correction is determined.

5. The method according to claim 4 and wherein said substantially simultaneous adjustment of the orientation and the power of the variable astigmatic optics is accomplished by the patient adjusting the orientation of the variable astigmatic optics and a servo mechanism adjusting the power of the variable astigmatic optics.

6. The method according to claim 4 and wherein said substantially simultaneous adjustment of the orientation and the power of the variable astigmatic optics is accomplished by the patient adjusting the power of the variable astigmatic optics and a servo mechanism adjusting the orientation of the variable astigmatic optics.

7. In a method for determining the refractive correction for an eye including the steps of:

providing corrective optics on a viewing axis between a patient's eye and a target location, said corrective optics comprising a unit having a plurality of lenses, axial movement of said unit providing variable spherical power, axial movement of at least one lens of said plurality of lenses providing variable astigmatic power in a direction normal to the axis and rotation of said unit about the axis providing rotation of said direction;

presenting, in alternate succession, first and second straight line targets in said target location, said first straight line target being presented with arbitrary meridional orientation without regard to any suspected principal meridian of the astigmatism of the patient's eye, and said second straight line target being presented with meridional orientation substantially 45° from the orientation of said first straight line target;

adjusting separately both said variable spherical power and said variable astigmatic power and direction to optimize the focus of the respective straight line target within the patient's eye;

the improvement comprising:

adjusting said variable spherical power, astigmatic power and direction for one of said first and second straight line targets, beginning the adjustment of the other of said first and second straight line targets from the astigmatic power and direction determined from the adjustment for said one of said first and second straight line targets; and coupling said astigmatic power adjustment to said direction adjustment whereby the dioptric power in the meridional orientation of the other of said first and second straight line targets is constant.

* * * * *

UNITED STATES PATENT AND TRADEMARK OFFICE
CERTIFICATE OF CORRECTION

PATENT NO.  : 4,105,303
DATED       : August 8, 1978
INVENTOR(S) : David L. Guyton It is certified that error appears in the above-identified patent and that said Letters Patent are hereby corrected as shown below:

In Column 2, line 45, after the word "sub-system" please delete the "." (period) and insert a --,-- (coma).

In Column 4, line 25, after the word "the" it should read --same--.

In Column 5, line 51, please change "100" to -- $\phi$ --.

In Column 6, line 23, please change the word "meridiant" to read --meridian--.

In Column 9, line 39, after the word "repeated" please insert a --)-- (parenthesis).

In Column 10, line 27, please change the word "His" to --his--.

In Column 11, line 27, please change the word "axis" to --axial--.

In Column 11, line 42, please change the word "or" to --of--.

In Column 12, line 59, after the word "second" please insert --adjustment--.

In Column 17, lines 20 and 22, please change the "[2P/C]" (brackets) to read --|2P/C|-- (straight vertical lines) at both occurrences.

Signed and Sealed this

Twenty-seventh Day of February 1979

[SEAL]

Attest:

RUTH C. MASON
Attesting Officer

DONALD W. BANNER
Commissioner of Patents and Trademarks